United States Patent
Sakaguchi et al.

[11] Patent Number: 5,131,390
[45] Date of Patent: Jul. 21, 1992

[54] DEVICE FOR CONTINUOUSLY MEASURING THE SKIN LOCAL SWEATING RATE

[75] Inventors: Masao Sakaguchi; Nobuyuki Ono, both of Nagano; Toshio Ohhashi, Matsumoto; Tomoya Kamei, Nagoya, all of Japan

[73] Assignees: Suzuken Co., Nagoya; Masao Sakaguchi, Nagano, both of Japan

[21] Appl. No.: 580,564

[22] Filed: Sep. 11, 1990

[30] Foreign Application Priority Data

Sep. 14, 1989 [JP] Japan ................................. 1-239604
Jan. 25, 1990 [JP] Japan ................................. 2-15378

[51] Int. Cl.$^5$ ............................................. A61B 5/00
[52] U.S. Cl. ..................................... 128/632; 128/760
[58] Field of Search ............... 128/630, 734, 760, 632; 73/29.01, 29.05, 25.04

[56] References Cited

U.S. PATENT DOCUMENTS

| | | | |
|---|---|---|---|
| 3,139,085 | 6/1964 | Custance et al. | 128/630 |
| 4,461,303 | 7/1984 | Refojo et al. | 73/29.01 |

FOREIGN PATENT DOCUMENTS

| | | | |
|---|---|---|---|
| 6357031 | 8/1986 | Japan . | |
| 3046131 | 2/1988 | Japan | 128/760 |

Primary Examiner—Lee S. Cohen
Assistant Examiner—J. R. Jastrzab
Attorney, Agent, or Firm—Dennison, Meserole, Pollack & Scheiner

[57] ABSTRACT

A device for continuously measuring the skin local sweating rate includes a capsule used for applying on a human skin at a measuring point and an air supply element for supplying dehumidified air to the capsule. A first chamber is formed between the capsule and the skin for receiving water vapor perspired from the skin and the dehumidified air supplied from the air supply element to produce the mixture of perspiration oriented water vapor through the skin and the dehumidified air. A second chamber is also formed within the capsule and connected with the first chamber through a communicating hole. The device further includes a humidity detecting element disposed in the second chamber. The humidity detecting element varies its electrical circuit constant according to the relative humidity of the mixture. A temperature detecting element is disposed in the second chamber for detecting the temperature in the second chamber and for outputting signals corresponding to the temperature. A humidity detecting signal output element is mounted on the capsule and is electrically connected with the humidity detecting element for outputting a humidity detecting signal corresponding to the circuit constant of the humidity detecting element. A calculation circuit calculates the sweating rate which is independent of the temperature of the mixture, based on the signals from the humidity detecting signal output element and the temperature detecting element. An element is provided for continuously recording the data of the sweating rate obtained by the calculation circuit.

6 Claims, 5 Drawing Sheets

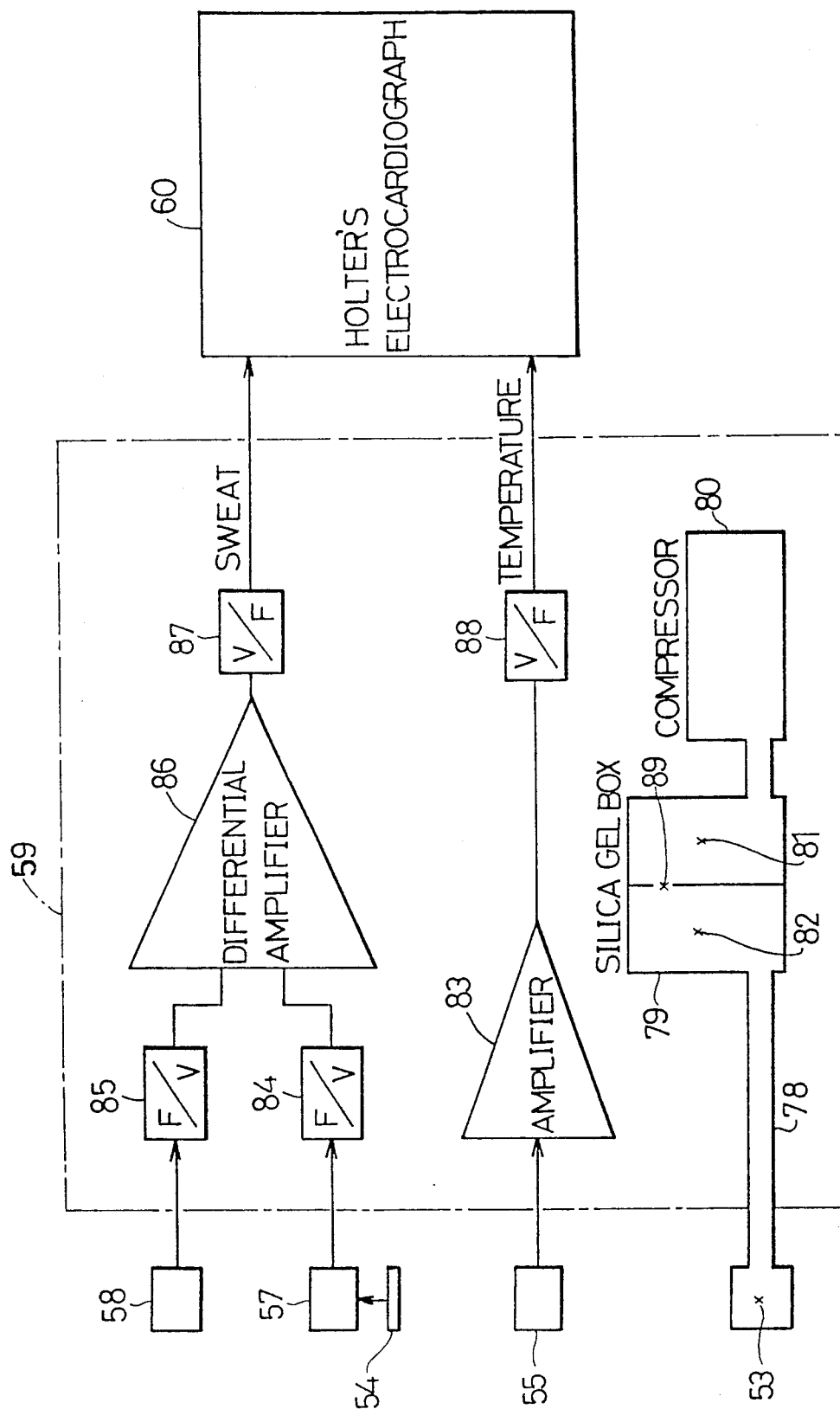

DEVICE FOR CONTINUOUSLY MEASURING THE SKIN LOCAL SWEATING RATE

BACKGROUND OF THE INVENTION

1. Field of the Invention

The present invention relates to a device for continuously measuring the skin local sweating rate including rate of emotional perspiration as well as that of heat-sensitive perspiration.

2. Description of the Prior Art

The devices for continuously measuring the skin local sweating rate are useful for a quantitative test of function of autonomic nervous system of a human body or sweating system for regulating body temperature, etc. Such devices are disclosed in Japanese Laid-Open Patent Publication Nos. 63-46131 and 63-57031.

The Japanese Laid-Open Patent Publication No. 63-46131 discloses a measuring device comprising a capsule and an air supply device. The capsule is applied on a skin at a sweating rate measuring point to form a chamber between the capsule and the skin. Air is supplied into the chamber from the air supply device, and the difference of the humidity of the air supplied into the chamber and discharged from the chamber is detected. The sweating rate at the measuring point is calculated based on the difference of the humidity thus detected.

The Japanese Laid-Open Patent Publication No. 63-57031 discloses a system comprising a dehumidifying device between a capsule and an air supply device. In this system, only one humidity sensor is required.

The prior art sweat measuring devices detect the relative humidity in the capsule, and the sweating rate is calculated on the assumption that the temperature of the capsule is invariable. However, the inventors of the present invention have proved that the influence of the variation in the capsule temperature cannot be neglected to obtain reliable sweating rate. Further, in these prior art devices, oscillators are fixed on the rear surfaces of the capsules and include the humidity detecting sensors as a circuit component, so that the frequency of the oscillators is varied according to not only the relative humidity but also to the temperature of the capsule and the temperature of the atmosphere. Therefore, accurate sweating rates could not be measured.

SUMMARY OF THE INVENTION

It is, accordingly, an object of the present invention to provide a device for continuously measuring the skin local sweating rate which can measure the sweating rate in such a manner that the sweating rate is independent of the temperature.

It is another object of the present invention to provide a device for continuously measuring the skin local sweating rate which can compensate variations in the output of a humidity detecting means caused by variations in temperature of its electric circuit.

It is a further object of the present invention to provide a device for continuously measuring the skin local sweating rate which can be used by a subject for daily measurement without rendering inconvenience or restriction.

It is a still further object of the present invention to provide a device for continuously measuring the skin local sweating rate which can utilize an existing means such as a Holter's electrocardiograph as an instrument for recording the measured data.

According to the present invention, there is provided a device for continuously measuring the skin local sweating rate comprising:

a capsule used for applying on a human skin at a measuring point;

air supply means for supplying dehumidified air to the capsule;

a first chamber formed between the capsule and the skin for receiving water vapor perspired from the skin and the dehumidified air supplied from the air supply means to produce the mixture of perspiration oriented water vapor and the dehumidified air;

a second chamber formed within the capsule and connected with the first chamber through a communicating hole;

humidity detecting means disposed in the second chamber and varying its electrical circuit constant according to the relative humidity of the mixture flown from the first chamber into the second chamber;

temperature detecting means disposed in the second chamber for detecting the temperature in the second chamber and for outputting signals corresponding to the temperature;

humidity detecting signal output means mounted on the capsule and electrically connected with the humidity detecting means for outputting a humidity detecting signal corresponding to the circuit constant of the humidity detecting means; and calculation means for calculating the sweating rate which is independent of the temperature, based on the signals from the humidity detecting signal output means and the temperature detecting means; and means for continuously recording the data of the sweating rate obtained by the calculation means.

In the present invention thus constructed, the water vapor perspired from the skin is uniformly diffused and mixed with the dehumidified air supplied from the air supply means in the first chamber of the capsule. The water contents in the mixture and its temperature is detected by the humidity detecting means and the temperature detecting means, respectively. The calculation means calculate the sweating rate which is independent of the temperature, based on the signals from the humidity detecting signal output means and the temperature detecting means. Thus the calculation means correct the relative humidity obtained from the humidity detecting signal output means to the real humidity, or the temperature independence of the signal from the humidity detecting signal output means is eliminated. Therefore, the continuous measurement of the sweating rate can be made easily and highly precisely.

The device may include temperature compensation signal output means disposed in the vicinity of the humidity detecting signal output means and having the same electrical construction and the same temperature characteristic as the humidity detecting signal output means. The temperature compensation signal output means outputs a temperature compensation signal substantially corresponding to the temperature of the humidity detecting signal output means. The temperature compensation signal is supplied to the calculation means so as to compensate the humidity detecting signal. Thus the calculation means compensate the temperature drift of the humidity detecting signal output means, and provide more accurate sweating rate.

A microprocessor can be employed as a main part of the calculation means so as to correct the relative humidity through its software and to display the sweating rate with a format to suit the purpose and to connect with an external general purpose computer. The systematization and the extension of the system can be made by employing the microprocessor.

Further, according to the present invention, there is provided a portable-type device for continuously measuring the skin local sweating rate comprising:

a capsule used for applying on a human skin at a measuring point;

air supply means for supplying dehumidified air to the capsule;

a first chamber formed between the capsule and the skin for receiving water vapor perspired from the skin and the dehumidified air supplied from the air supply means to produce the mixture of the perspiration oriented water vapor and the dehumidified air;

a second chamber formed within the capsule and connected with the first chamber through a communicating hole;

humidity detecting means disposed in the second chamber and varying its electrical circuit constant according to the relative humidity of the mixture flown from the first chamber into the second chamber;

temperature detecting means disposed in the second chamber for detecting the temperature in the second chamber and for outputting a temperature detecting signal corresponding to the temperature;

humidity detecting signal output means mounted on the capsule and electrically connected with the humidity detecting means for outputting a humidity detecting signal corresponding to the circuit constant of the humidity detecting means;

a portable box having the air supply means therein; and portable record means for continuously recording information concerning a function of a human body on detachable recording media for a long time, so that the humidity detecting signal and the temperature detecting signal can be recorded on the portable record means.

The device of this portable-type may be incorporated in a total system comprising:

regeneration means for regenerating and demodulating the signals recorded on the detachable recording media;

calculation means for calculating the sweating rate which is independent of the temperature of the mixture from the signals demodulated by the regeneration means; and means for continuously recording and displaying the data of the sweating rate obtained by said calculation means.

The system of this type can be generally divided into two sections one of which is sweat measuring and recording section, and the other of which is regeneration and displaying section. The sweat measuring and recording section may constitute a portable section. For this purpose, the air supply means disposed in the portable box may include a compressor of relatively small size so as to save energy. The portable box may include therein the electric circuit for processing the output signals from the humidity detecting means and the temperature detecting means disposed within the capsule. For recording the relative humidity and the temperature, an existing recording means such as a Holter's electrocardiograph which permits recording for a long time is available. The recorded data is regenerated by the regeneration means and may be processed by the calculation means such as a microprocessor. Thus the system of this type permits daily continuous measurement of the sweating rate without rendering restriction to the subject.

In the case that the Holter's electrocardiograph has been used as a recording means, the electrocardiogram can be also recorded simultaneously with the above data. Further, in this case, an approach to diagnosis of the cardiac function can be made using the sweating rate as a barometer by displaying the cardiogram together with the sweating rate.

The device of the present invention can be used in the field of clinical medicine and sport medicine for testing the function of autonomic nervous system of human body or the function of regulation of body temperature. The device can be also used in the field of the subsistence stores for testing the influence of vaporization of water on a cosmetic etc. or the migration of the water in clothing. Particularly in the clinical application, the device can be used for evaluation of the effect of medicines, or for judgment of the effect of the rehabilitation remedy.

The invention will become more fully apparent from the claims and the description as it proceeds in connection with the drawings.

BRIEF DESCRIPTION OF THE DRAWINGS

FIG. 5 is a diagram showing several circuits incorporated in the portable box shown in FIG. 4.

DETAILED EXPLANATION OF THE PREFERRED EMBODIMENT

Figure 1:
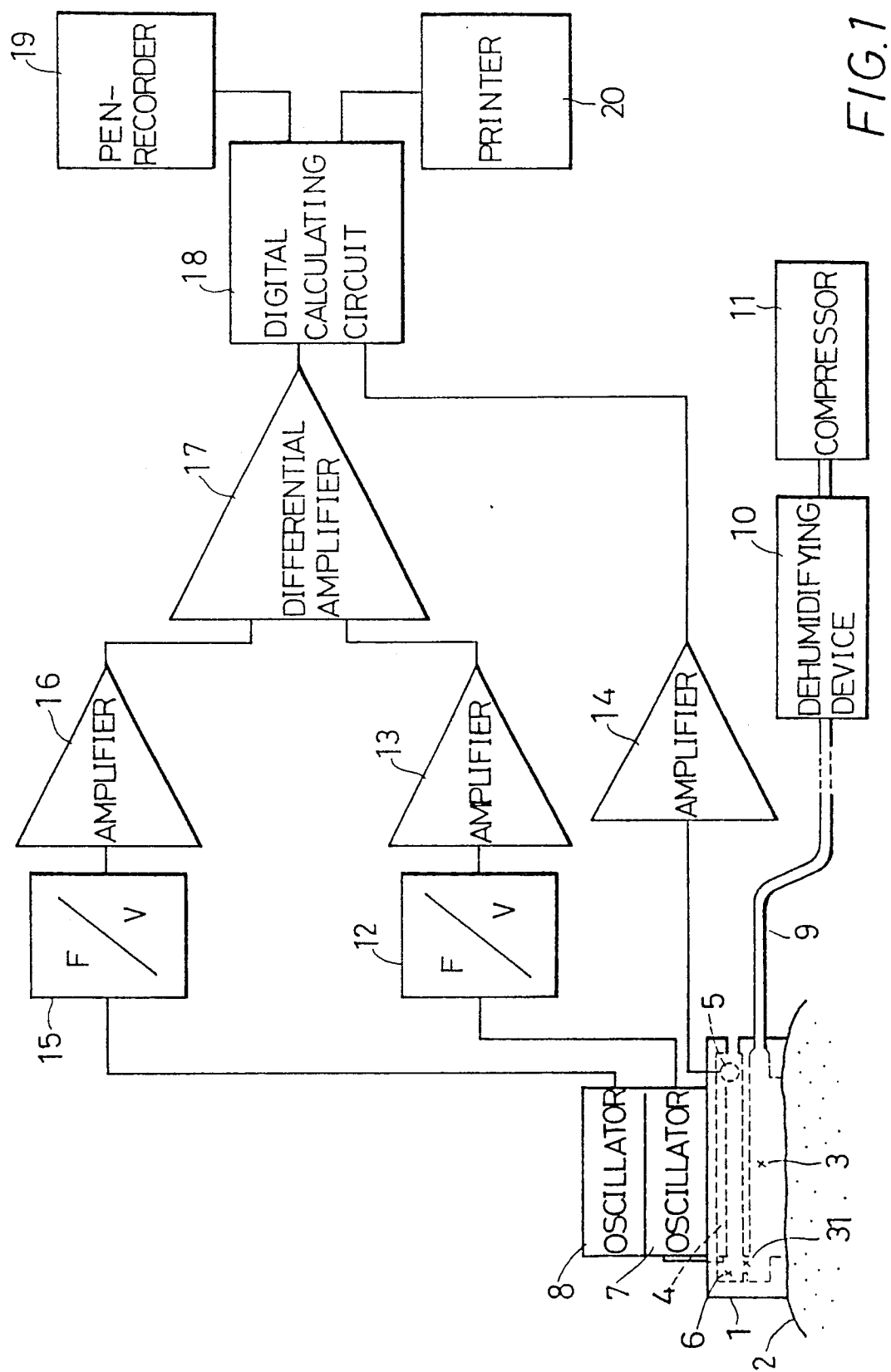
FIG. 1 is a block diagram showing a device for continuously measuring the skin local sweating rate according to a first embodiment of the present invention.
Figure 2:
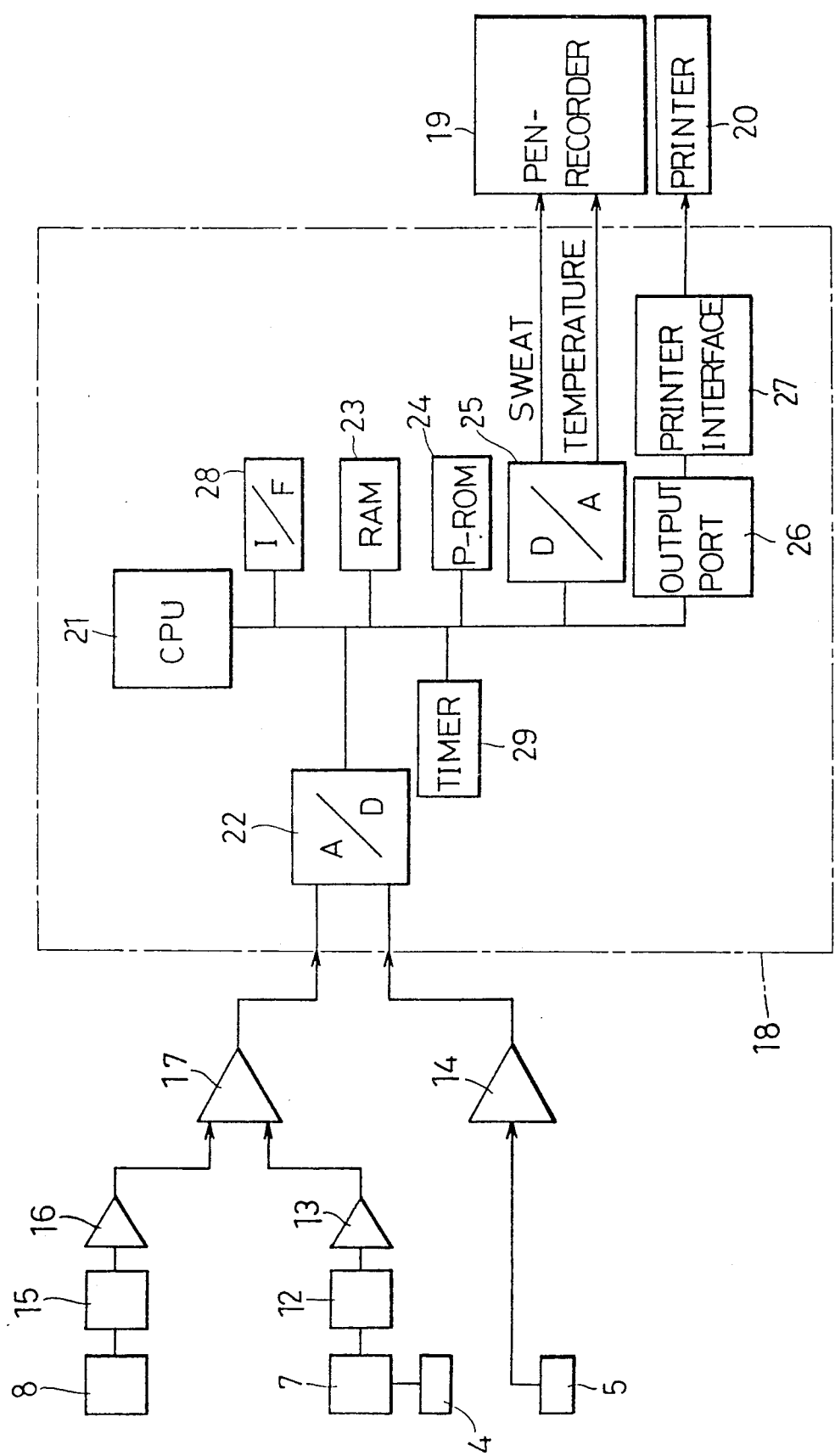
FIG. 2 is a diagram showing the digital calculating circuit of the device shown in FIG. 1.
Figure 3:
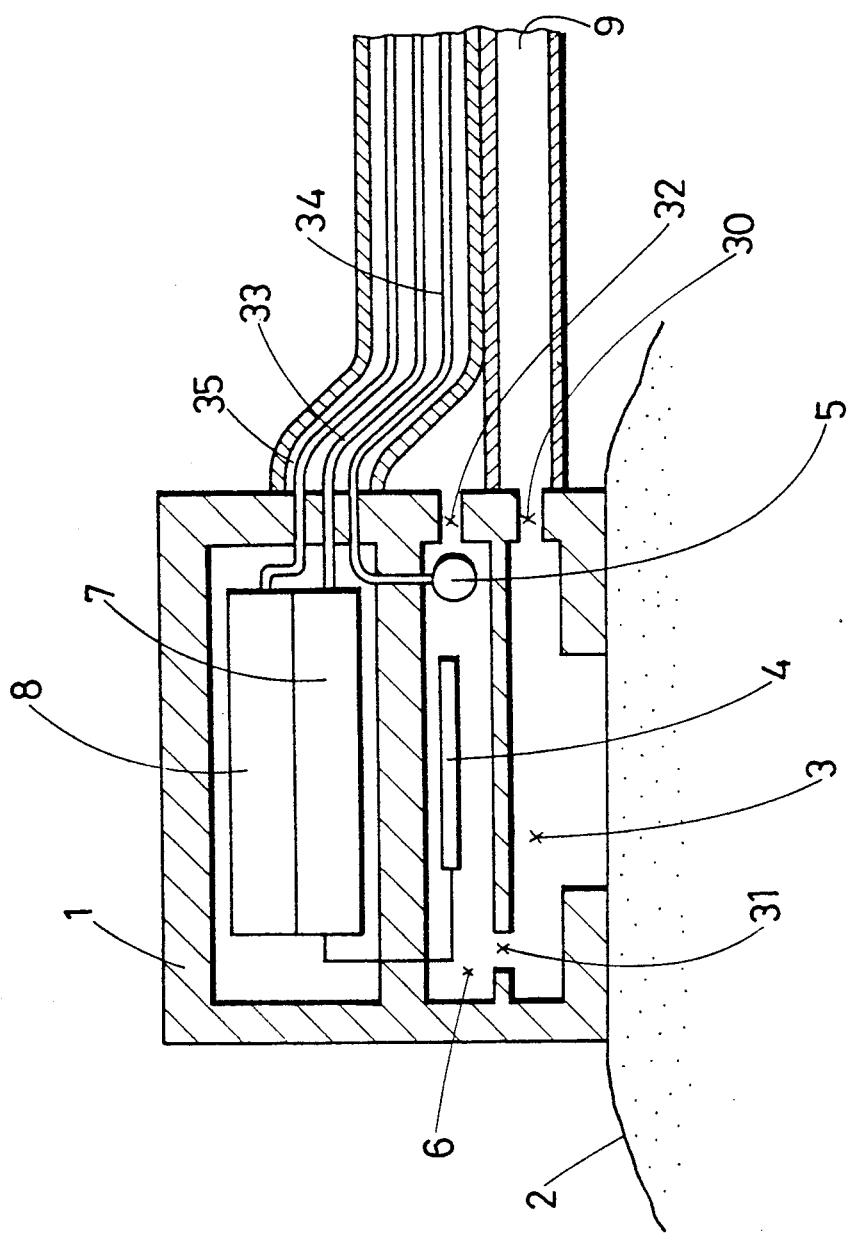
FIG. 3 is an enlarged sectional view of the capsule shown in FIG. 1.

Referring to FIGS. 1 to 3, there is shown a device for continuously measuring the skin local sweating rate according to a first embodiment of the present invention. As shown in FIGS. 1 and 3, a capsule 1 is applied on a human skin 2 at a measuring point, and a first chamber 3 is formed between the capsule 1 and the skin 2. Within the capsule 1, a second chamber 6 is formed next to the first chamber 3, and both chambers 3 and 6 are communicated through a communication hole 31. The first chamber 3 produces a diffused mixture of perspiration oriented water vapor and a dehumidified air. The second chamber 6 includes therein a humidity sensor 4 and a temperature sensor 5. The humidity sensor 4 is electrically connected with a first oscillator 7. The first chamber 3, the humidity sensor 4, the temperature sensor 5, the second chamber 6 and the first oscillator 7 form a detecting section for detecting the sweating rate and the temperature. A second oscillator 8 is disposed on the same substrate as the first oscillator 7 and forms a temperature compensation section for the first oscillator 7. An air supply section for supplying the dehumidified air is formed by an air channel 9, a dehumidifying device 10 having silica gel and a compressor 11 therein.

A processing section of a detected signal of sweating rate is formed by a first F/V converter 12 and a first amplifier 13 connected with the first oscillator 7. A temperature measuring section of the diffused mixture is formed by a second amplifier 14. An output section of a temperature compensation signal is formed by a second F/V converter 15 and a third amplifier 16 connected with the second oscillator 8. The other circuits subsequent to a differential amplifier 17 form a differential operational section, a data processing section and a recording and displaying section, respectively, as will be hereinafter explained.

The first chamber 3 of the capsule 1 has an opening, so that the capsule 1 can closely contact the skin 2 at the opening. The humidity sensor 4 disposed within the second chamber 6 is a capacitance type sensor such as a ceramic humidity sensor which varies its electric capacity according to the relative humidity of the diffused mixture produced in the first chamber 3. Such variation is immediately converted into variation in the frequency of the first oscillator 7, and is subsequently converted by the first F/V converter 12 into the voltage according to the frequency. The voltage thus obtained is amplified by the first amplifier 13, so that the output voltage of the first amplifier 13 corresponds to the sweating rate from the skin 2 superposing the ingredient caused by the variation in the temperature of the electric circuit forming the first oscillator 7. The second oscillator 8 is disposed on the same substrate as the first oscillator 7 and the circuit constant of the second oscillator 8 is so determined that the temperature characteristic of the electric circuit forming the second oscillator 8 is the same as that of the electric circuit of the first oscillator 7. Therefore, the frequency of the second oscillator 8 varies in the same manner as the frequency of the second oscillator 8 depending on the temperature. The output signal of the second oscillator 8 is supplied to the differential amplifier 17 through the second F/V converter 15 and the third amplifier 16. The output voltage of the differential amplifier 16 thus corresponds to the sweating rate from the skin 2 eliminating the ingredient caused by the variation in temperature of the first oscillator 7. The output of the differential amplifier 16 is processed by a digital calculating circuit 18 together with the output of the second amplifier 14 which corresponds to the temperature of the diffused mixture detected by the second amplifier 14, so that the sweating rate and the temperature variation of the capsule 1 is recorded by a pen-recorder 19, and the total amount of sweat during a predetermined test period, and the average sweating rate and the frequency of sweating during a unit of time are printed as digital values by a printer 20.

Referring to FIG. 2, the circuit diagram of the digital calculating circuit 18 is shown in detail. The digital calculating circuit 18 includes a CPU (microprocessor) 21 as a main part. The output of the differential amplifier 17 corresponding to the relative humidity and the output of the second amplifier 14 corresponding to the temperature of the diffused mixture are converted into digital values by an A/D converter 22 and are stored in RAM 23 as measured data. The CPU 21 corrects the measured data so as to obtain the absolute sweating rate which is independent of the temperature, and linearizes the same based on a calculation program and a calculation table which are written in a P-ROM 24. The CPU 21 further calculates the total amount of sweat during a predetermined test period, the average sweating rate and the frequency of sweating during a unit of time, the temperature of the capsule 1, etc. which are stored in the RAM 23 as calculated data. The calculated data concerning the sweating rate and the temperature of the capsule 1 stored in the RAM 23 is converted into analogue data by a D/A converter 25 and is recorded by the pen-recorder 19. The calculated data can be directly transmitted to the printer 20 through an output port 26 and a printer interface 27, so that they can be printed as digital data by the printer 20. The printer 20 may print the other digital data than the calculated data. All the data can be supplied to an external general purpose computer through a serial interface 28 which is connected with a data bus. A timer 29 administrates the period of measurement, the time of measuring, etc.

The detecting section for detecting the sweat and the temperature shown in FIG. 1 will be hereinafter described with reference to FIG. 3. The capsule 1, the first chamber 3, the humidity sensor 4, the second chamber 6 and the oscillator 7 form a sweat detecting section. On the other hand, an inlet port 30, a communicating hole 31 connecting the first chamber 3 with the second chamber 6, an outlet port 32 and the air channel 9 form an air supply passage. The water vapor perspired from the skin 2 and filled in the first chamber 3 is diffused and mixed with the dehumidified air supplied from the air channel 9 through the inlet port 30. The diffused mixture flows into the second chamber 6 through the communication hole 31 and thereafter flows out of the capsule 1 through the outlet port 32. As the sweating rate varies, the capacitance of the humidity sensor 4 disposed within the second chamber 6 also varies, and consequently the frequency of the first oscillator 7 varies. The output of the first oscillator 7 is supplied via a line 33 to the first F/V converter 12 and thereafter to the first amplifier 13. The output of the first amplifier 13, therefore, corresponds to the relative humidity of the diffused mixture in the second chamber 6. On the other hand, the temperature sensor 5 disposed in the second chamber 6 outputs the voltage signal based on the variation of its resistance. The output of the temperature sensor 5 is supplied to the second amplifier 14, so that the output of the second amplifier 14 corresponds to the temperature in the second chamber 6. The second oscillator 8 is disposed on the same substrate as the first oscillator 7 and is connected to the second F/V converter 15 via a line 35 and subsequently to the third amplifier 13. The variation in the output voltage of the third amplifier 13, therefore, corresponds to the variation in the frequency of the second oscillator 8 caused by the temperature variation in the electric circuit forming the second oscillator 8.

Figure 4:
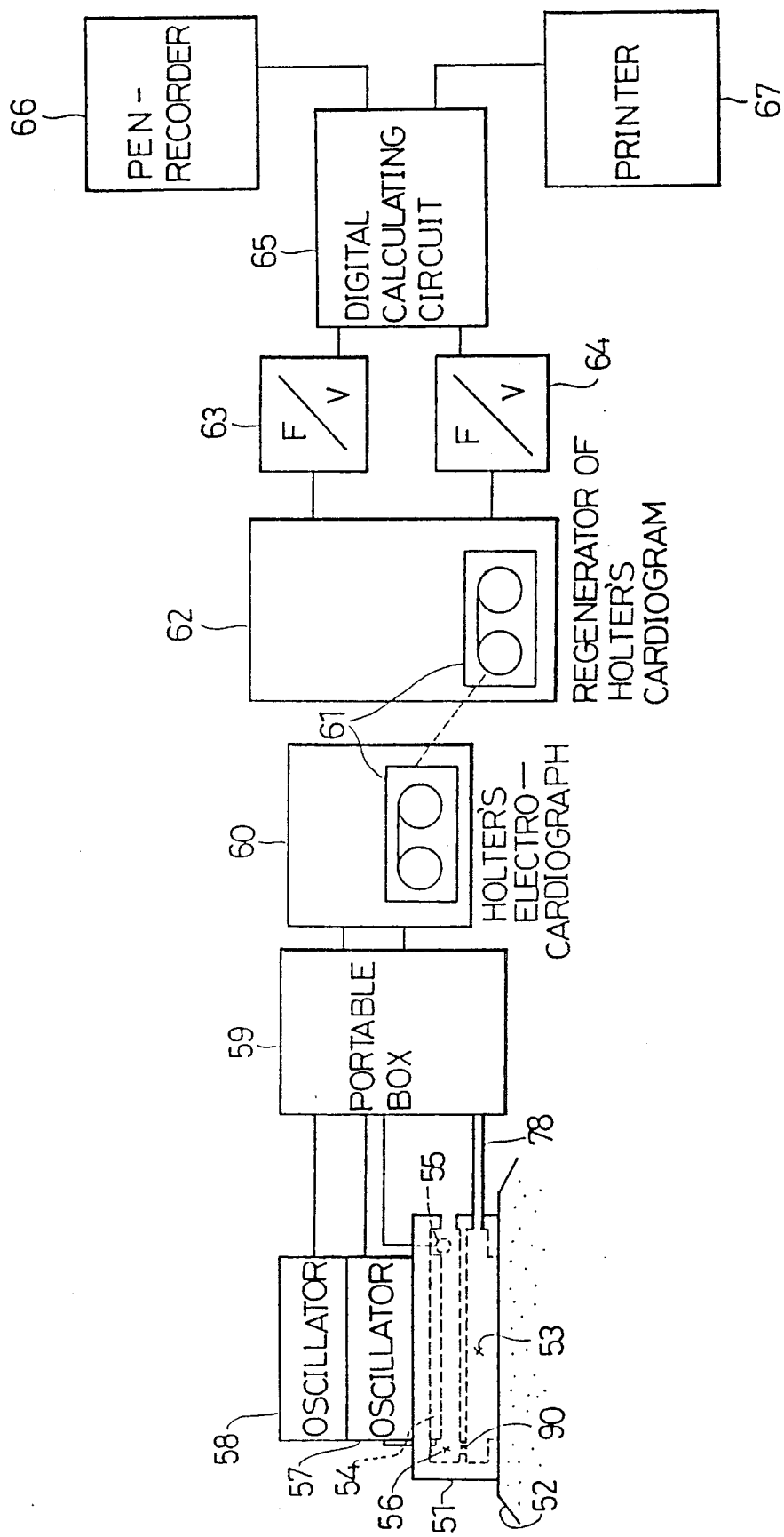
FIG. 4 is a block diagram showing a device for continuously measuring the skin local sweating rate according to a second embodiment of the present invention.

Referring to FIGS. 4 and 5, shown therein is a device for continuously measuring the skin local sweating rate according to a second embodiment of the present invention.

As shown in FIG. 4, a capsule 51 of relatively small size has a first chamber 53 and a second chamber 56. The first chamber 53 produces a diffused mixture of sweat or water vapor and a dehumidified air. The second chamber 56 includes therein a humidity sensor 54 and a temperature sensor 55. The humidity sensor 54 is electrically connected with a first oscillator 57. The first chamber 53, the humidity sensor 54, the temperature sensor 55, the second chamber 56 and the first oscillator 57 form a detecting section for detecting the sweating rate and the temperature. A second oscillator 58 is disposed on the same substrate as the first oscillator 57 and forms a temperature compensation section of the first oscillator 57. A portable box 59 accommodates an electric circuit for processing the data signal from the first oscillator 57, the second oscillator 58 and the temperature sensor 55 as will be hereinafter explained. The portable box 59 also accommodates air supply means for supplying a dehumidified air to the first chamber 53 of the capsule 51 through an air channel 78. A Holter's electrocardiograph 60 constitutes a long-time recording section and records on a micro cassette tape 61 the detected signal corresponding to the sweating rate and the detected signal corresponding to the temperature of the mixture which have been modulated into low frequency by the electric circuit in the portable box 59. The holter's electrocardiograph 60 as well as the capsule 51 and the portable box 59 are portable by a subject of the test. On the other hand, a regenerator 62 of Holter's cardiogram for regenerating the signal recorded on the micro cassette tape 61, a first and a second F/V converter 63, 64 for demodulation, a digital calculating circuit 65, a pen-recorder 66 and a printer 67 which are connected with the regenerator 62 are stationarily disposed.

The first chamber 53 of the capsule 51 has an opening, so that the capsule 51 can closely contact a skin 52 of a human body at the opening. The humidity sensor 54 disposed within the second chamber 56 is of a capacitance type, and its electric capacity varies with the relative humidity of the diffused mixture which has been produced in the first chamber 53 and enters the second chamber 56 through a communicating hole 90. Such variation is immediately converted into the variation in the frequency of the first oscillator 57. The second oscillator 58 is disposed on the same substrate as the first oscillator 57 and the frequency of the second oscillator 58 varies in the same manner as the frequency of the first oscillator 57 which depends on the temperature. The temperature sensor 55 is disposed in the second chamber 56 and detects the temperature of the diffused mixture. The output signals of the first and second oscillators 57, 58 are received by the electric circuit within the portable box 58, which modulates these signals into low frequency, and are recorded on the micro cassette tape 61 set in the Holter's electrocardiograph 60 as modulated signals corresponding to the sweating rate. The output signal of the temperature sensor 55 is also received and modulated by the electric circuit within the portable box 58 and is thereafter recorded in the micro cassette tape recorder 61 of Holter's electrocardiograph 60 as a modulated signal corresponding to the temperature. After the measurement of the sweating rate, the micro cassette tape 61 ejected from the Holter's electrocardiograph 60 is set in the regenerator 62 of Holter's cardiogram. The regenerator 62 regenerates the modulated signals corresponding to the sweating rate and the temperature recorded in the micro cassette tape 61 at high speed. The regenerated signals are demodulated into the variation in voltage by the first and second F/V converters 63, 64. The digital calculating circuit 65 corrects the demodulated signal to obtain the real sweating rate which is independent of the temperature, and calculates the total amount of sweat during a predetermined test period, the average sweating rate and the frequency of sweating during a unit of time, and the temperature of the capsule 51. The pen-recorder 66 records the data concerning the variation in the absolute sweating rate and the temperature. The printer 67 prints as digital values the total amount of sweat during a predetermined test period, and the average sweating rate and the frequency of sweating during a unit of time.

The construction of the portable box 59 and the operation of the electric circuit disposed therein will be hereinafter explained with reference to FIG. 5.

The first oscillator 57 outputs a signal which includes the ingredient caused by the variation in the temperature of the diffused mixture superposed on the ingredient caused by the variation in the temperature of the first oscillator 57 itself. The second oscillator 58 outputs a signal which includes the ingredient caused by the variation in the temperature of the oscillator 58 itself. The output of the first and second oscillators 57, 58 are changed into the voltage by the first and second F/V converters 84, 85, respectively, and are supplied to a differential amplifier 86 so as to be differentially amplified. The differential amplifier 86 thus outputs a signal corresponding to the sweating rate from the skin 52 in which the ingredient corresponding to the variation in the temperature of the first oscillator 57 has been eliminated. The output of the differential amplifier 86 is modulated by a third V/F converter 87 into low frequency such as 10 to 100 Hz for recording on the micro cassette tape 61 set in the Holter's electrocardiograph 60. The output of the temperature sensor 55 which detects the temperature of the diffused mixture in the second chamber 56 is amplified by an amplifier 83 and thereafter modulated into low frequency by a fourth V/F converter 88.

The air supplied from a compressor 80 of small size is dehumidified by a silica gel box 79 and is supplied to the first chamber 53 of the capsule 51 through the air channel 78. The silica gel box 79 has two chambers 81 and 82 which are separated from each other and are connected in series through a small communicating hole 89, so that the air can be effectively dehumidified.

In this embodiment, the micro cassette tape 61 set in the Holter's electrocardiograph 60 may also record the data concerning the cardiogram as well as the data concerning the sweating rate and the temperature. Further, an IC card, etc. can be used as recording means other than the Holter's electrocardiograph 60. Additionally, data concerning the blood pressure, respiration, etc. may be simultaneously recorded with the data concerning the cardiogram, so that the diagnosis of function of human body can be effectively performed.

While the invention has been described with reference to preferred embodiments thereof, it is to be understood that modification or variation may be easily made without departing from the scope of the present invention which is defined by the appended claims.

What is claimed is:

1. A device for continuously measuring the skin local sweating rate comprising:
   a capsule used for applying on a human skin at a measuring point;
   air supply means for supplying dehumidified air to said capsule;
   a first chamber formed between said capsule and the skin for receiving water vapor perspired from the skin and the dehumidified air supplied from said air supply means and for producing a mixture of perspiration oriented water vapor through the skin and the dehumidified air;
   a second chamber formed within said capsule and connected with said first chamber through a communicating hole;

humidity detecting means disposed in said second chamber and varying its electrical circuit constant according to the relative humidity of the mixture flown from said first chamber into said second chamber;

temperature detecting means disposed in said second chamber for detecting the temperature in said second chamber and for outputting signals corresponding to the temperature;

humidity detecting signal output means mounted on said capsule and electrically connected with said humidity detecting means for outputting a humidity detecting signal corresponding to the circuit constant of said humidity detecting means; and calculation means for calculating the sweating rate which is independent of the temperature of the mixture, based on the signals from said humidity detecting signal output means and said temperature detecting means; and means for continuously recording the data of the sweating rate obtained by said calculation means.

2. The device as defined in claim 1 further including temperature compensation signal output means disposed in the vicinity of said humidity detecting signal output means and having the same electrical construction and the same temperature characteristic as said humidity detecting signal output means, said temperature compensation signal output means outputting a temperature compensation signal substantially corresponding to the temperature of said humidity detecting signal output means, said temperature compensation signal being supplied to said calculation means so as to compensate said humidity detecting signal.

3. A device for continuously measuring the skin local sweating rate comprising:
   a capsule used for applying on a human skin at a measuring point;
   air supply means for supplying dehumidified air to said capsule;
   a first chamber formed between said capsule and the skin for receiving water vapor perspired from the skin and the dehumidified air supplied from said air supply means and for producing a mixture of perspiration oriented water vapor through the skin and the dehumidified air;
   a second chamber formed within said capsule and connected with said first chamber through a communicating hole;
   humidity detecting means disposed in said second chamber and varying its electrical circuit constant according to the relative humidity of the mixture flown from said first chamber into said second chamber;
   temperature detecting means disposed in said second chamber for detecting the temperature in said second chamber and for outputting a temperature detecting signal corresponding to the temperature;
   humidity detecting signal output means mounted on said capsule and electrically connected with said humidity detecting means for outputting a humidity detecting signal corresponding to the circuit constant of said humidity detecting means;
   a portable box having said air supply means therein; and
   portable record means for continuously recording information concerning a function of a human body on detachable recording media for a long time, so that said humidity detecting signal and said temperature detecting signal can be recorded on said portable record means.

4. The device as defined in claim 3 further including:
   temperature compensation signal output means disposed in the vicinity of said humidity detecting signal output means and having the same electrical construction and the same temperature characteristic as said humidity detecting signal output means, said temperature compensation signal output means outputting a temperature compensation signal substantially corresponding to the temperature of said humidity detecting signal output means so as to compensate for temperature drift of said humidity detecting signal.

5. A system for continuously measuring the skin local sweating rate for a long time comprising: a portable section including
   a capsule used for applying on a human skin at a measuring point,
   air supply means for supplying dehumidified air to said capsule,
   a first chamber formed between said capsule and the skin for receiving water vapor perspired from the skin and the dehumidified air supplied from said air supply means and for producing a mixture of perspiration oriented water vapor through the skin and the dehumidified air,
   a second chamber formed within said capsule and connected with said first chamber through a communicating hole,
   humidity detecting means disposed in said second chamber and varying its electrical circuit constant according to the relative humidity of the mixture flown from said first chamber into said second chamber,
   temperature detecting means disposed in said second chamber for detecting the temperature in said second chamber and for outputting a temperature detecting signal corresponding to the temperature,
   humidity detecting signal output means mounted on said capsule and electrically connected with said humidity detecting means for outputting a humidity detecting signal corresponding to the circuit constant of said humidity detecting means,
   a portable box having said air supply means therein, and
   portable record means for continuously recording information concerning a function of a human body on detachable recording media for a long time, so that said humidity detecting signal and said temperature detecting signal can be recorded on said portable record means; and a stationary section including
   regeneration means for regenerating and demodulating said signals recorded on said detachable recording media,
   calculation means for calculating the sweating rate, which is independent of the temperature of the mixture from said signals demodulated by said regeneration means, and
   means for continuously recording and indicating the data of the sweating rate obtained by said calculation means.

6. The system as defined in claim 5 wherein said portable section further includes temperature compensation signal output means disposed in the vicinity of said humidity detecting signal output means and having the same electrical construction and the same temperature characteristic as said humidity detecting signal output means, said temperature compensation signal output means outputting a temperature compensation signal substantially corresponding to the temperature of said humidity detecting signal output means, said temperature compensation signal being supplied to said calculation means so as to compensate said humidity detecting signal.

* * * * *